US011191710B2

(12) United States Patent
Olivier-Mabilais et al.

(10) Patent No.: US 11,191,710 B2
(45) Date of Patent: Dec. 7, 2021

(54) PHOTOPROTECTIVE COSMETIC COMPOSITION AND PROCESS FOR OBTAINING THE SAME

(71) Applicant: L'OREAL, Paris (FR)

(72) Inventors: Sandrine Olivier-Mabilais, Cheville Larue (FR); Yasuko Nagamatsu, Kanagawa (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/064,141

(22) PCT Filed: Dec. 23, 2016

(86) PCT No.: PCT/EP2016/082634
§ 371 (c)(1),
(2) Date: Jun. 20, 2018

(87) PCT Pub. No.: WO2017/109213
PCT Pub. Date: Jun. 29, 2017

(65) Prior Publication Data
US 2019/0000738 A1 Jan. 3, 2019

(30) Foreign Application Priority Data

Dec. 23, 2015 (FR) ..................... 15 63268

(51) Int. Cl.
A61K 8/49 (2006.01)
A61Q 17/04 (2006.01)
A61K 8/58 (2006.01)
A61K 8/44 (2006.01)
A61K 8/73 (2006.01)
A61K 8/37 (2006.01)
A61K 8/86 (2006.01)
A61K 8/81 (2006.01)

(52) U.S. Cl.
CPC ............ *A61K 8/4966* (2013.01); *A61K 8/375* (2013.01); *A61K 8/445* (2013.01); *A61K 8/585* (2013.01); *A61K 8/73* (2013.01); *A61K 8/8158* (2013.01); *A61K 8/86* (2013.01); *A61Q 17/04* (2013.01)

(58) Field of Classification Search
None
See application file for complete search history.

(56) References Cited

U.S. PATENT DOCUMENTS

| 2,463,264 | A |   | 3/1949  | Graenacher et al. |
|-----------|---|---|---------|-------------------|
| 5,166,355 | A |   | 11/1992 | Leistner et al.   |
| 5,237,071 | A |   | 8/1993  | Leistner et al.   |
| 5,624,663 | A |   | 4/1997  | Deflandre et al.  |
| 5,730,993 | A |   | 3/1998  | Allard            |
| 5,951,993 | A | * | 9/1999  | Scholz ............. A61K 8/342 424/405 |
| 6,225,467 | B1 |   | 5/2001  | Esteghamatian et al. |
| 2007/0154415 | A1 | * | 7/2007 | Dahms ............... A61K 8/26 424/59 |
| 2010/0111884 | A1 |   | 5/2010 | Acker et al. |
| 2011/0045069 | A1 | * | 2/2011 | Ley .................. A61K 31/216 424/474 |

FOREIGN PATENT DOCUMENTS

| DE | 197 26 184 A1 | 12/1998 |
| DE | 197 46 654 | 2/1999 |
| DE | 197 55 649 A1 | 6/1999 |
| DE | 101 62 844 A1 | 7/2003 |
| EP | 0 133 981 A2 | 3/1985 |
| EP | 0 669 323 A1 | 8/1995 |
| EP | 0 775 698 A1 | 5/1997 |
| EP | 0 832 642 A2 | 4/1998 |
| EP | 0 893 119 A1 | 1/1999 |
| EP | 0 967 200 A1 | 12/1999 |
| EP | 1 008 586 A1 | 6/2000 |
| EP | 1 027 883 A2 | 6/2000 |
| EP | 1 133 980 A2 | 9/2001 |
| EP | 1 300 137 A2 | 4/2003 |
| GB | 191207068 A | 5/1913 |
| GB | 2 206 339 A | 1/1989 |
| GB | 2 303 549 A | 2/1997 |
| WO | WO 93/04665 A1 | 3/1993 |
| WO | WO 2004/006878 A1 | 1/2004 |
| WO | WO 2004/085412 A2 | 10/2004 |
| WO | WO 2005/058269 A1 | 6/2005 |
| WO | WO 2006/032741 A1 | 3/2006 |
| WO | WO 2006/034982 A1 | 4/2006 |
| WO | WO 2006/034985 | 4/2006 |

(Continued)

OTHER PUBLICATIONS

Ceralution H: retrieved from: https://www.stobec.com/data/produit/1496~v~data_8403.pdf. Retrieved on Sep. 20, 2019.*
Duynhoven et al.: Microstructural investigation of monoglyceride-water coagel systems by NMR and CryoSEM, Journal of Colloid and Interface Science, vol. 285, Issue 2, May 2, 2005, p. 703-710.*
Sein et al., "Rheological Characterization, Crystallization, and Gelation Behavior of Monoglyceride Gels", Journal of Colloid and Interface Science, 249, 412-422 (2002).

(Continued)

*Primary Examiner* — Hong Yu

(74) *Attorney, Agent, or Firm* — Polsinelli PC

(57) ABSTRACT

The invention relates to a composition, in particular a cosmetic composition, characterized in that it comprises:—at least one monoglyceride,—at least one tartaric ester of monoglycerides based on C12-C22,—at least one UV filter,—at least one HLB surfactant greater than 10, and—at least one hydrophilic gelling agent wherein the content of said one or more surfactant(s) having a HLB greater than 10 is comprised between 0.2% and 10% by weight, based on the total weight of the composition.

20 Claims, No Drawings

(56) References Cited

FOREIGN PATENT DOCUMENTS

| WO | WO 2006/034991 A1 | 4/2006 | |
|---|---|---|---|
| WO | WO 2006/034992 A1 | 4/2006 | |
| WO | WO 2006/035000 A1 | 4/2006 | |
| WO | WO 2006/035007 A1 | 4/2006 | |
| WO | WO 2014/023640 A2 | * | 2/2014 |
| WO | WO 2014/135666 A1 | * | 9/2014 |
| WO | WO 2014/207066 A1 | * | 12/2014 |
| WO | WO-2014/207068 A1 | 12/2014 | |
| WO | WO 2015/014818 A2 | 2/2015 | |

OTHER PUBLICATIONS

Chupin et al., "Lipid organization and dynamics of the monostearoyglycerol-water system. A $^2$H NMR study", Chemistry and Physics of Lipids, 109, 15-28 (2001).

Cassin et al., "Investigation of the Gel to Coalgel Phase Transition in Monoglyceride-Water Systems", Langmuir 14, 5757-5763 (1998).

Heertje et al., "Liquid Crystalline Phases in the Structuring of Food Products", Article No. fs980369, Lebensm.-Wiss. u.-Technol., 31, 387-396 (1998).

Kirk-Othmer, Encyclopedia of Chemical Technology, Third Edition, vol. 22, Surfactants and Detersive Systems, pp. 332-432 (1983).

William C. Griffin, "Calculation of HLB Values of Non-Ionic Surfactants", presented at the May 14, 1954 Meeting, NYC, Journal of the Society of Cosmetic Chemists, 249-256.

J. Falbe (Editor), "Surfactants in Consumer Products—Theory, Technology and Application" TRAD GB, 4.4 Surfactant Aggregates, pp. 1-4 and 175-176, Oct. 1986.

Hou Haiyuan (Editor), "Physical Chemistry Fundamentals of Surfactants, Chapter 5 Characteristic of Surfactant Solutions: Orderliness", pp. 107-108, Aug. 2014.

\* cited by examiner

PHOTOPROTECTIVE COSMETIC COMPOSITION AND PROCESS FOR OBTAINING THE SAME

CROSS REFERENCE TO RELATED APPLICATIONS

This application is the National Phase of Application No. PCT/EP2016/082634 filed Dec. 23, 2016, which claims priority to Application No. 15 63268 filed in France on Dec. 23, 2015 under 35 U.S.C. § 119. The entire contents of each application are hereby incorporated by reference.

The present invention relates to a photoprotective cosmetic composition and process for obtaining the same.

The harmful effect of the rays of the sun on the skin has been known for a long time. Solar radiation in particular comprises UV radiation able to provoke an alteration of the skin. This alteration of the skin can be immediate through the appearance of burns or appear in the longer term by provoking a premature aging and the possible appearance of skin cancers. It is therefore desirable to protect the skin from solar rays.

For this, it is necessary to use solar filters, applied onto the skin for example by the intermediary of different formulations such as for example creams, oils, milks or sticks.

In order to obtain high solar protection, the filters are introduced into the creams at a high concentration, which constitutes a first technical problem since it is sought to limit their presence.

In addition, the high concentration of solar filters provokes the degradation of the quality of the textures of the various formulations, in particular creams, oils, milks or sticks for example, as the latter become more greasy.

This also generates an observance problem. Indeed, consumers who are not very seduced by these textures do not sufficiently reapply the cream during the day, as such decreasing the photoprotection of the skin and not fighting against the harmful effects of the rays of the sun.

There is therefore a need to lower the content in filters in the formulations, as for example creams, while maintaining the level of protection against the rays of the sun.

The invention in particular has for purpose to solve the technical problem consisting in decreasing the content in solar filters in the compositions while still maintaining the level of solar protection.

The invention also has for purpose to solve the technical problem consisting in improving the solar protection procured by compositions, in particular cosmetic, and more particularly emulsions, such as for example sun creams.

Moreover, the invention has for purpose to solve the technical problem consisting in supplying photoprotective cosmetic compositions of which the texture is pleasant and/or comfortable for the user, in particular when being felt on the skin.

The invention also has for purpose to solve the technical problem of the observance relative to the application of photoprotective cosmetic compositions.

The invention also has for purpose to solve the technical problem consisting in providing a photoprotective cosmetic composition that is stable over time also making it possible to solve the problems mentioned hereinabove.

The invention also has for purpose to provide a method for manufacturing a photoprotective cosmetic composition that makes it possible to solve the problems mentioned hereinabove.

Finally, the invention has for purpose to solve at least one of, preferably all of these technical problems, in an industrial, reliable and reproducible manner.

Surprisingly, the inventors discovered that it was possible to achieve at least one and preferably all of the aforementioned objectives thanks to a composition, in particular cosmetic, characterized in that it comprises:
  at least one monoglyceride,
  at least one tartaric ester of monoglycerides of fatty acids,
  at least one UV filter,
  at least one surfactant having a HLB greater than 10, and
  at least one hydrophilic gelling agent.

The inventors in particular surprisingly discovered that such a composition made it possible to obtain a substantial improvement of the sun protection factor. The sun protection factor is in particular measured by the value of SPF, which is measured according to standardized methods, for example in vitro or in vivo. The value of SPF obtained for such a composition is higher than that expected.

As such, in order to achieve the same high level of photoprotection, such a composition requires a less substantial quantity of filters, which also makes it possible to obtain a less greasy texture. In addition, at equal quantities of filters, the composition according to the invention has a texture that is less greasy and results in a less substantial greasy effect on the skin.

According to the invention, the HLB (Hydrophilic-Lipophilic Balance is a value that is characteristic of a surfactant. The value of HLB allows to quantify the balance that exists between the hydrophilic portion and the lipophilic portion of the surfactant molecule. The higher this value is, the more hydrophilic the surfactant is. The HLB value as per GRIFFIN is defined in J. Soc. Cosm. Chem. 1954 (volume 5), pages 249-256.

Reference may be made to the document "Encyclopedia of Chemical Technology, KIRK-OTHMER", volume 22, p. 333-432, $3^{rd}$ edition, 1979, WILEY, for the definition of the properties and emulsifying functions of surfactant agents, in particular p. 347-377 of this reference, for non-ionic surfactant agents.

In terms of this invention, SPF (Sun Protection Factor) means the sun protection factor that is measured by standardized methods.

According to a first aspect, the invention relates to a composition, in particular a cosmetic composition, characterized in that it comprises:
  at least one monoglyceride,
  at least one tartaric ester of monoglycerides based on C12-C22 fatty acids,
  at least one UV filter,
  at least one surfactant having a HLB greater than 10, and
  at least one hydrophilic gelling agent.

Advantageously, the composition comprises an aqueous phase.

Preferably, the composition according to the invention contains a coagel phase.

Aqueous systems based on the combination of monoglycerides and a tartaric ester of monoglycerides, are commonly known as coagels and have been used in food for a few years now to make lighter margarines. A coagel generally comprises a three-dimensional matrix containing a non-aqueous continuous phase. A coagel is a complex system that is generally comprised of percolated fatty body crystals in an aqueous phase. Such a three-dimensional architecture can contain up to 98% of an aqueous phase.

These systems have undergone significant structural studies. Mention may be made of the following articles, among others:

Liquid Crystalline Phases in the Structuring of Food Products, 1998, Lebensmittel-Wissenschaft und-technologie, 31, 387-396, Investigation of the Gel to Coagel Phase Transition in Monoglyceride-Water Systems (Langmuir 1998, 14, 5757-5763)

Lipid organization and dynamics of the monostearoylglycerol-water system. A 2H NMR study (Chemistry and Physics of lipids 109 (2001) 15-28)

Rheological Characterization, Crystallization, and Gelation (Behavior of Monoglyceride Gels (Journal of Colloid and Interface Science 249, (2002) 412-422).

In the coagel architecture, the capacity for incorporating water into the lamellar phase (constituted of water and of monoglyceride) can be improved by adding a small quantity of anionic surfactant which creates electrostatic repulsions between the blades. This step allows for an optimized swelling in such a way as to obtain a gel of acceptable consistency.

The use of monoglyceride stearate in cosmetics for stabilizing emulsions has long been known. However, the use of a tartaric ester of monoglyceride is less common.

The compositions according to the invention are preferably in the form of creams, milks, oils, foams, sprayable compositions or sticks. It is important to note that the compositions according to the invention, if they have the appearance of cosmetic creams have, when observed under a microscope, a structure different from conventional emulsions characterized for example by a regular carpet of droplets. The compositions according to the invention are characterized in particular by a highly birefringent appearance in polarized light which is typical of their semi-crystalline nature.

In this application, the percentages of the constituents are given in mass relative to the total mass of the composition, unless mentioned otherwise.

Monoglyceride

A monoglyceride, or monoacylglycerol (MAG), is a monoester of fatty acid and of glycerol. They can be classified into two groups, 1-monoacyglycerols and 2-monoacylglycerols according to whether the acyl group is in position 1 or 2 of the glycerol residue. In particular, said at least one monoglyceride is different from said at least one tartaric ester of monoglycerides based on C12-C22 fatty acids as mentioned below.

According to a particular embodiment, the composition comprises as a monoglyceride one or more monoglycerides comprising an alkyl chain, saturated or unsaturated, comprising from 12 to 22 carbon atoms.

Preferably, the monoglyceride comprises an alkyl chain, saturated or unsaturated, comprising 16 to 18 carbon atoms.

In this case, interest is particularly given to 1-monoacylglycerols, such as those of the following formula (e.g. C18):

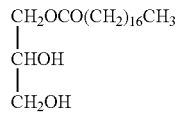

The length of the fatty acid chain can range from C12 to C22. Preferentially, monoesters of C16 or C18 fatty acids and glycerol are chosen.

The raw material used is important in that the monoglycerides used allow a coagel phase to be formed. Monoglycerides containing less than 10% residual diglycerides are in particular used. The use of monoglyceride stearates is preferred (INCI name: GLYCERYL STEARATE), for example marketed under the name HP DIMODAN by DANISCO company or those sold under the name TEGIN 90 by the company EVONIK GOLDSCHMIDT.

The composition according to the invention comprises monoglyceride content from 1% to 20%, preferably from 2 to 10% and very preferably from 3 to 8% by weight based on the total weight of said composition.

Tartaric Ester of Monoglycerides of Fatty Acids

Tartaric esters of monoglycerides of fatty acids are usually obtained by esterifying at position 3 of a 1-monoacylglycerol with tartaric acid that is possibly acylated (C2-C4) at positions 2 and 3. The length of the fatty acid chain can range from C12 to C22, preferably esters of C16 or C18 monoglycerides will be chosen.

The tartaric ester of monoglyceride is preferably a diacetyl tartaric acid ester and of monoglyceride comprising an alkyl chain, saturated or unsaturated, comprising from 12 to 22 carbon atoms, and preferably comprising 16 or 18 carbon atoms.

According to an embodiment the tartaric ester of monoglyceride of fatty acids of the composition according to the invention is a diacetyl tartaric ester of monoglyceride comprising an alkyl chain, saturated or unsaturated, comprising from 12 to 22 carbon atoms, and preferably comprising 16 or 18 carbon atoms.

In this case, particular interest is given to diacetyl tartaric acid esters of C18 monoglycerides, such as those of the following formula:

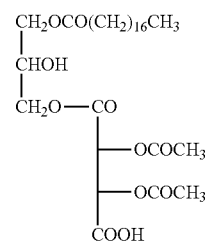

The invention covers the various isomers of tartaric acid and mixtures thereof, including racemic mixtures.

These ingredients and their uses are described on pages 88-95 of the Functional Ingredients for Food brochure published by DANISCO and available on the http://www.danisco.com/ site.

These esters can be chosen among tartaric ester of mono- and diglycerides of fatty acids (E472d additive), and a monoacetyltartric ester and diglycerides of fatty acids (E472e additive). Monoglycerides and diglycerides esters with a purity of about 80% or more are mainly sought.

Tartaric ester or esters of monoglycerides of fatty acids can be used with INCI name: DIACETYL TARTARIC ACID ESTERS OF MONO AND DIGLYCERIDES OF FATTY ACIDS (of which the shortened name can be "DATEM").

According to an embodiment, the tartaric ester of monoglycerides content of the composition according to the invention is from 0.05% to 2%, preferably from 0.1 to 1% and very preferably from 0.1 to 0.5% by weight based on the total weight of the composition.

UV Filter(s)

The UV filters of the composition according to the invention can be of different natures.

They can be organic, lipophilic, hydrophilic or insoluble.

The term "lipophilic UV filter" refers to any cosmetic or dermatological filter liable to be completely dissolved in the molecular state in a liquid fat phase or be solubilized in colloidal form (for example in micellar form) in a liquid fat phase.

The term "hydrophilic UV filter" refers to any cosmetic or dermatological filter liable to be completely dissolved in the molecular state in a liquid aqueous phase or be solubilized in colloidal form (for example in micellar form) in a liquid aqueous phase.

The term "insoluble UV filter" refers to any cosmetic or dermatological filter which is not defined as a lipophilic UV filter or as a hydrophilic UV filter, in particle form in liquid aqueous or fat phase.

The UV filters of the composition according to the invention can provide a UVA and/or UVB photoprotection.

According to an embodiment, the composition can comprise one or several bis-resorcinyl triazine derivatives such as described and prepared according to the syntheses indicated in patent applications EP-A-0775 698.

Examples of such compounds suitable for use include:
2,4-bis {[4-(2-ethyl-hexyloxy)-2-hydroxy]-phenyl}-6-(4-methoxy-phenyl)-1,3,5-triazine;
2,4-bis{[4-(3-(2-propyloxy)-2-hydroxy-propyloxy)-2-hydroxy]-phenyl}-6-(4-methoxyphenyl)-1,3,5-triazine;
2,4-bis {[4-(2-ethyl-hexyloxy)-2-hydroxy]-phenyl}-6-[4-(2-methoxyethyl-carboxyl)-phenylamino]-1,3,5-triazine;
2,4-bis {[4-tris(trimethylsiloxy-silylpropyloxy)-2-hydroxy]-phenyl}-6-(4-methoxyphenyl)-1,3,5-triazine;
2,4-bis {[4-(2"-methylpropenyloxy)-2-hydroxy]-phenyl}-6-(4-methoxyphenyl)-1,3,5-triazine;
2,4-bis {[4-(1',1',1',3',5',5',5'-heptamethyltrisiloxy-2"-methylpropyloxy)-2-hydroxy]-phenyl}-6-(4-methoxy-phenyl)-1,3,5-triazine.
2,4-bis{[4-(3-(2-propyloxy)-2-hydroxy-propyloxy]-2-hydroxy]-phenyl}-6-[(4-ethylcarboxyl)-phenylamino]-1,3,5-triazine;
2,4-bis {[4-(2-ethyl-hexyloxy)-2-hydroxy]-phenyl}-6-(1-methylpyrrol-2-yl)-1,3,5-triazine.

More specifically, at least the compound 2,4-bis {[4-(2-ethyl-hexyloxy)-2-hydroxy]-phenyl}-6-(4-methoxy-phenyl)-1,3,5-triazine or Bis-Ethylhexyloxyphenol Methoxyphenyl Triazine (INCI name) such as the product sold under the trade name "TINOSORB S" by CIBA GEIGY can be used.

According to one embodiment, the composition may comprise one or several dibenzoylmethane derivatives. Particularly mention may be made of, but is not limited to:
2-methyldibenzoylmethane,
4-methyldibenzoylmethane,
4-isopropyldibenzoylmethane,
4-tert.-butyldibenzoylmethane,
2,4-dimethyldibenzoylmethane,
2,5-dimethyldibenzoylmethane,
4,4'-diisopropyldibenzoylmethane,
4,4'-dimethoxydibenzoylmethane,
4-tert.-butyl-4'-methoxydibenzoylmethane,
2-methyl-5-isopropyl-4'-methoxydibenzoylmethane,
2-methyl-5-tert-butyl-4'-methoxydibenzoylmethane,
2,4-dimethyl-4'-methoxydibenzoylmethane,
2,6-dimethyl-4-tert-butyl-4'-methoxydibenzoylmethane.

According to one embodiment, the composition may comprise one or several benzylidene camphor derivatives. Mention can be made in particular of:
3-Benzylidene camphor manufactured under the name "MEXORYL SD" by CHIMEX,
4-Methylbenzylidene camphor sold under the name "EUSOLEX 6300" by MERCK,
Benzylidene Camphor Sulfonic Acid manufactured under the name "MEXORYL SL" by CHIMEX,
Camphor Benzalkonium Methosulfate manufactured under the name "MEXORYL SO" by CHIMEX,
Polyacrylamidomethyl Benzylidene Camphor manufactured under the name "MEXORYL SW" by CHIMEX.
Terephthalylidene Dicamphor Sulfonic Acid marketed under the name MEXORYL SX by CHIMEX.

The organic UV filters can also be selected from anthranilics; cinnamic derivatives; salicylic derivatives; benzophenone derivatives; phenyl benzotriazole derivatives; benzalmalonate derivatives particularly those cited in the patent U.S. Pat. No. 5,624,663; phenyl benzimidazole derivatives; imidazolines; 4,4-diarylbutadiene derivatives; bis-benzoazolyle derivatives as described in the patents EP669323 and U.S. Pat. No. 2,463,264; p-aminobenzoic acid (PABA) derivatives; methylene bis-(hydroxyphenyl benzotriazole) derivatives as described in the applications U.S. Pat. Nos. 5,237,071, 5,166,355, GB2303549, DE 197 26 184 and EP893119; benzoxazole derivatives as described in the patent applications EP0832642, EP1027883, EP1300137 and DE10162844; filter polymers and filter silicones such as those particularly described in the application WO-93/04665; dimers derived from—alkylstyrene such as those described in the patent application DE19855649; 4,4-diarylbutadienes as described in the applications EP0967200, DE19746654, DE19755649, EP-A-1008586, EP1133980 and EP133981; other merocyanine derivatives such as those described in WO04006878, WO05058269 and WO06032741 and the mixtures thereof.

As examples of organic UV filters used in the composition according to the invention, include those referred to hereinafter using the INCI name thereof:

Lipophilic UV-A Filters

Dibenzoylmethane Derivatives

Isopropyl Dibenzoylmethane; Butyl Methoxydibenzoylmethane

Aminobenzophenones n-hexyl 2-(4-diethylamino-2-hydroxybenzoyl)-benzoate particularly sold under the trade name "UVINUL A+" by BASF;
1,1'-(1,4-piperazinedil)bis[1-[2-[4-(diethylamino)-2-hydroxybenzoyl]phenyl]-methanone (CAS 919803-06-8)

According to a preferred embodiment the composition according to the invention comprises the UV filter of INCI name diethylamino hydroxybenzoyl hexyl benzoate (sold for example under the trade name "UVINUL A+")

Anthranilic Derivatives

Menthyl anthranilate particularly sold under the trade name "NEO HELIOPAN MA" by SYMRISE;

4,4-diarylbutadiene Derivatives 1,1-dicarboxy (2,2'-dimethyl-propyl)-4,4-diphenylbutadiene;

Merocyanine Derivatives

Octyl-5-N,N-diethylamino-2-phenysulfonyl-2,4-pentadienoate;

According to a particular embodiment the composition according to the invention comprises Butyl Methoxydibenzoylmethane (also known under the name Avobenzone).

Hydrophilic UV-A Filters

The bis-benzoazolyl derivatives as described in the patents EP 669 323, and U.S. Pat. No. 2,463,264 and more specifically the compound Disodium Phenyl Dibenzimidazo tetrasulfonate sold under the trade name "NEO HELIOPAN AP" by SYMRISE;

According to a particular embodiment the composition according to the invention comprises Terephtalylidene Dicamphor Sulfonic Acid, (sold for example under the trade name Mexoryl SX).

Lipophilic UV-B Filters

Para-aminobenzoates

Ethyl PABA;
Ethyl Dihydroxypropyl PABA;
Ethylhexyl Dimethyl PABA (ESCALOL 507 from ISP);

Salicylic Derivatives

Homosalate particularly sold under the name "Eusolex HMS" by Rona/EM Industries;
Ethylhexyl Salicylate particularly sold under the name "NEO HELIOPAN OS" by SYMRISE;
Dipropyleneglycol Salicylate particularly sold under the name "DIPSAL" by SCHER;
TEA Salicylate sold under the name "NEO HELIOPAN TS" by SYMRISE;

Cinnamates

Ethylhexyl Methoxycinnamate particularly sold under the trade name "PARSOL MCX" by DSM Nutritional Products, Inc.;
Isopropyl Methoxy cinnamate;
Isoamyl Methoxy cinnamate particularly sold under the trade name "NEO HELIOPAN E 1000" by SYMRISE;
Diisopropyl Methylcinnamate;
Cinnoxate;
Glyceryl Ethylhexanoate Dimethoxycinnamate;

β,β'-diphenylacrylate Derivatives

Etocrylene, particularly sold under the trade name "UVINUL N35" by BASF;
Octocrylene, particularly sold under the trade name "UVINUL N539" by BASF;

Benzylidene Camphor Derivatives

3-Benzylidene camphor manufactured under the name "MEXORYL SD" by CHIMEX;
Methylbenzylidene camphor sold under the name "EUSOLEX 6300" by MERCK;
Polyacrylamidomethyl Benzylidene Camphor manufactured under the name "MEXORYL SW" by CHIMEX;

Triazine Derivatives

Ethylhexyl triazone particularly sold under the trade name "UVINUL T150" by BASF;
Diethylhexyl Butamido Triazone particularly sold under the trade name "UVASORB HEB" by SIGMA 3V;
2,4,6-tris(4'-amino benzalmalonate of dineopentyle)-s-triazine;
2,4,6-tris(diisobutyl 4'-amino benzalmalonate)-s-triazine;
2,4-bis(dineopentyl 4'-amino benzalmalonate)-6-(n-butyl 4'-aminobenzoate)-s-triazine;
2,4-bis(n-butyl 4'-amino benzoate)-6-(aminopropyltrisiloxane)-s-triazine;
the symmetrical triazine filters described in the patent U.S. Pat. No. 6,225,467, the application WO 2004/085412 (see compounds 6 and 9) or the document "Symmetrical Triazine Derivatives" IP.COM Journal, IP.COM INC. WEST HENRIETTA, N.Y., US (Sep. 20, 2004) particularly 2,4,6-tris-(biphenyl)-1,3,5-triazine (particularly 2,4,6-tris(biphenyl-4-yl-1,3,5-triazine) and 2,4,6-tris(terphenyl)-1,3,5-triazine, the latter two filters being described in the BEIERSDORF applications WO 06/035000, WO 06/034982, WO 06/034991, WO 06/035007, WO 2006/034992, WO 2006/034985).

Imidazoline Derivatives

Ethylhexyl Dimethoxybenzylidene Dioxoimidazoline Propionate,

Benzalmalonate Derivatives

Polyorganosiloxanes with a benzalmalonate function such as Polysilicone-15 particularly sold under the trade name "PARSOL SLX" by DSM Nutritional Products, Inc.;
Di-neopentyl 4'-methoxybenzalmalonate;

According to a particular embodiment the composition according to the invention comprises one or several UV filters chosen from the following filters: Ethylhexylsalicylate (sold in particular under the name "NEO HELIOPAN OS" by SYMRISE); Octocrylene (sold in particular under the trade name "UVINUL N539" by BASF); Ethylhexyl triazone (sold in particular under the trade name "UVINUL T150") and any mixtures thereof.

Hydrophilic UV-B Filters

The Following p-aminobenzoic Acid (PABA) Derivatives

PABA,
Glyceryl PABA and
PEG-25 PABA particularly sold under the trade name "UVINUL P25" by BASF.
Phenylbenzimidazole Sulfonic Acid particularly sold under the trade name "EUSOLEX 232" by MERCK,
ferulic acid,
salicylic acid,
DEA methoxycinnamate,
Benzylidene Camphor Sulfonic Acid manufactured under the name "MEXORYL SL" by CHIMEX,
Camphor Benzalkonium Methosulfate manufactured under the name "MEXORYL SO" by CHIMEX,

V/Combined Lipophilic UVA and UVB Filters

Benzophenone Derivatives

Benzophenone-1 particularly sold under the trade name "UVINUL 400" by BASF;
Benzophenone-2 particularly sold under the trade name "UVINUL D50" by BASF;
Benzophenone-3 or Oxybenzone particularly sold under the trade name "UVINUL M40" by BASF;
Benzophenone-6 particularly sold under the trade name "Helisorb 11" by Norquay;
Benzophenone-8 particularly sold under the trade name "Spectra-Sorb UV-24" by American Cyanamid;
Benzophenone-10;
Benzophenone-11;
Benzophenone-12;

Phenyl Benzotriazole Derivatives

Drometrizole Trisiloxane particularly sold under the name "Silatrizole" by RHODIA CHIMIE or manufactured under the name "Meroxyl XL" by CHIMEX;
Methylene bis-Benzotriazolyl Tetramethylbutylphenol, sold in solid form particularly under the trade name "MIXXIM BB/100" by FAIRMOUNT CHEMICAL or in micronized form in aqueous dispersion particularly under the trade name "TINOSORB M" by CIBA SPECIALTY CHEMICALS;

According to a particular embodiment the composition according to the invention comprises one or several UV filters chosen from the following filters: Drometrizole Trisiloxane (sold in particular under the name "Silatrizole" by RHODIA CHIMIE or manufactured under the name "Meroxyl XL" by the company CHIMEX), Methylene bis-Benzotriazolyl Tetramethylbutylphenol possibly in micronized form and any of the mixtures thereof.

Benzoxazole Derivatives 2,4-bis-[5-1(dimethylpropyl)benzoxazol-2-yl-(4-phenyl)-imino]-6-(2-ethylhexyl)-imino-1,3,5-triazine particularly sold under the name Uvasorb K2A by Sigma 3V.

V/Combined Hydrophilic UVA and UVB Filters

Benzophenone derivatives comprising at least one sulfonic radical such as Benzophenone-4 particularly sold under the trade name "UVINUL MS 40" by BASF,
Benzophenone-5 and
Benzophenone-9.

According to an embodiment, the composition comprises one or several UV filters chosen from Terephtalylidene Dicamphor Sulfonic Acid, Butyl Methoxydibenzoylmethane, Drometrizole Trisiloxane, Octocrylene, Ethylhexylsalicylate, Methylene bis-Benzotriazolyl Tetramethylbutylphenol, Ethylhexyl triazone, Bis-Ethylhexyloxyphenol Methoxyphenyl Triazine, diethylamino hydroxybenzoyl hexyl benzoate and any of the mixtures thereof.

According to an embodiment, the composition comprises at least one organic UV filter chosen from among the following: Drometrizole Trisiloxane, Ethylhexyl triazone and diethylamino hydroxybenzoyl hexyl benzoate and any of the mixtures thereof. It can further comprise one or several filters of a non-organic nature, for example mineral.

According to one embodiment, the composition may comprise one or several lipophilic UV filters.

The quantity of the UV filter or filters, present in the composition according to the invention, may range from 0.1 to 50% by weight in relation to the total weight of the composition. It preferably ranges from 10 to 50% by weight, preferentially from 20 to 50% by weight, and better yet ranges from 20 to 40% by weight, in relation to the total weight of the composition. In one embodiment, it ranges from 1 to 20% by weight, preferentially from 5 to 20% by weight, in relation to the total weight of the composition.

According to an embodiment, the Terephtalylidene Dicamphor Sulfonic Acid content of the composition according to the invention is from 3 to 12%, based on the total weight of the composition.

According to an embodiment, the Butyl Methoxydibenzoylmethane content of the composition according to the invention is from 1 to 5%, based on the total weight of the composition.

According to an embodiment, the Drometrizole Trisiloxane content of the composition according to the invention is from 1 to 4%, possibly from 2 to 3% based on the total weight of the composition.

According to an embodiment, the Octocrylene content of the composition according to the invention is from 0.5 to 2.5%, based on the total weight of the composition.
According to an embodiment, the Ethylhexylsalicylate content of the composition according to the invention is from 2 to 8%, based on the total weight of the composition.

According to an embodiment, the Methylene bis-Benzotriazolyl Tetramethylbutylphenol content of the composition according to the invention is from 1 to 4%, based on the total weight of the composition.

According to an embodiment, the Ethylhexyl triazone content of the composition according to the invention is from 1 to 4%, possibly from 2 to 3%, based on the total weight of the composition.

According to an embodiment, the Bis-Ethylhexyloxyphenol Methoxyphenyl Triazine content of the composition according to the invention is from 0.5 to 4.5%, based on the total weight of the composition.

According to an embodiment, the diethylamino hydroxybenzoyl hexyl benzoate content of the composition according to the invention is from 0.5 to 5%, possibly from 1 to 4% based on the total weight of the composition.

The UV filters of the composition according to the invention can be of a mineral nature. The mineral UV filters of the composition according to the invention can be surface treated. The surface treatment can be total or partial. The surface agent may be hydrophilic, hydrophobic or lipophobic The composition according to the invention may comprise mineral filters which are pigments. The pigments may be coated or uncoated.

The coated pigments are pigments which have undergone one or a plurality of chemical, electronic, mechanochemical and/or mechanical surface treatments with compounds as described for example in Cosmetics & Toiletries, February 1990, Vol. 105, p. 53-64, such as amino acids, beeswax, fatty acids, fatty alcohols, anionic surfactants, lecithins, sodium, potassium, zinc, iron or aluminum salts of fatty acids, metal (titanium or aluminum) alkoxides, polyethylene, silicones, proteins (collagen, elastin), alkanolamines, silicon oxides, metal oxides or sodium hexametaphosphate.

It is known that the silicones are organosilicate polymers or oligomers with a linear or cyclic, branched or cross-linked structure, with a variable molecular weight, obtained by polymerization and/or polycondensation of suitably functionalized silanes, and essentially consisting of a repetition of primary structural units wherein the silicon atoms are interconnected by oxygen atoms (siloxane bond), optionally substituted hydrocarbon radicals being directly bound via a carbon atom on said silicon atoms.

The term "silicones" also covers the silanes required for the preparation thereof, particularly, alkyl silanes.

The silicones used for coating pigments suitable for the present invention are preferably selected from the group containing alkyl silanes, polydialkylsiloxanes, and polyalkylhydrogen siloxanes. More preferentially, the silicones are selected from the group containing octyl trimethyl silane, polydimethylsiloxanes and polymethylhydrogen siloxanes.

Obviously, prior to the treatment thereof with silicone, the metal oxide pigments may have been treated with other surface agents, particularly cerium oxide, alumina, silica, aluminum compounds, silicon compounds, or mixtures thereof.

The coated pigments are, for example, titanium oxides coated with:
silica such as the product "SUNVEIL" from IKEDA and the product "Eusolex T-AVO" from MERCK or the product "Sunsil Tin 50" from SUNJIL Chemical.—
silica and iron oxide such as the product "SUNVEIL F" from IKEDA,
silica and alumina such as the products "MICROTITANIUM DIOXIDE MT 500 SA" and "MICROTITANIUM DIOXIDE MT 100 SA" from TAYCA, "TIOVEIL" from TIOXIDE, and "Mirasun TiW 60" from Rhodia,
alumina such as the products "TIPAQUE TTO-55 (B)" and "TIPAQUE TTO-55 (A)" from ISHIHARA, and "UVT 14/4" from KEMIRA,
alumina and aluminum stearate such as the product "MICROTITANIUM DIOXIDE MT 100 TV, MT 100 TX, MT 100 Z, MT-01" from TAYCA, the products "Solaveil CT-10 W", "Solaveil CT 100" and "Solaveil CT 200" from UNIQEMA,
silica, alumina and alginic acid such as the product "MT-100 AQ" from TAYCA,
alumina and aluminum laurate such as the product "MICROTITANIUM DIOXIDE MT 100 S" from TAYCA,
iron oxide and iron stearate such as the product "MICROTITANIUM DIOXIDE MT 100 F" from TAYCA,
zinc oxide and zinc stearate such as the product "BR351" from TAYCA,
silica and alumina and treated with a silicone such as the products "MICROTITANIUM DIOXIDE MT 600 SAS", "MICROTITANIUM DIOXIDE MT 500 SAS" or "MICROTITANIUM DIOXIDE MT 100 SAS" from TAYCA,
silica, alumina, aluminum stearate and treated with a silicone such as the product "STT-30-DS" from TITAN KOGYO,
silica and treated with a silicone such as the product "UV-TITAN X 195" from KEMIRA, or the product SMT-100 WRS from TAYCA.
alumina and treated with a silicone such as the products "TIPAQUE TTO-55 (S)" from ISHIHARA, or "UV TITAN M 262" from KEMIRA,
triethanolamine such as the product "STT-65-S" from TITAN KOGYO,
stearic acid such as the product "TIPAQUE TTO-55 (C)" from ISHIHARA,
sodium hexametaphosphate such as the product "MICROTITANIUM DIOXIDE MT 150 W" from TAYCA.

Further titanium oxide pigments treated with a silicone are for example $TiO_2$ treated with octyl trimethyl silane such as that sold under the trade name "T 805" by DEGUSSA SILICES, $TiO_2$ treated with a polydimethylsiloxane such as that sold under the trade name "70250 Cardre UF TiO2SI3" by CARDRE, anatase/rutile $TiO_2$ treated with a polydimethylhydrogen siloxane such as that sold under the trade name "MICRO TITANIUM DIOXIDE USP GRADE HYDROPHOBIC" by COLOR TECHNIQUES.

The uncoated titanium oxide pigments are for example sold by TAYCA under the trade names "MICROTITANIUM DIOXIDE MT 500 B" or "MICROTITANIUM DIOXIDE MT600 B", by DEGUSSA under the name "P 25", by WACKHER under the name "Oxyde de titane transparent PW", by MIYOSHI KASEI under the name "UFTR", by TOMEN under the name "ITS" and by TIOXIDE under the name "TIOVEIL AQ".

The uncoated zinc oxide pigments are for example
those marketed under the name "Z-cote" by Sunsmart;
those marketed under the name "Nanox" by Elementis;
those marketed under the name "Nanogard WCD 2025" by Nanophase Technologies;
The coated zinc oxide pigments are for example
those marketed under the name "Z-COTE HP1" by SUNSMART (ZnO coated with dimethicone);
those marketed under the name "CS-5 zinc oxide" by Toshibi (ZnO coated with polymethylhydrogen siloxane);
those marketed under the name "Nanogard Zinc Oxide FN" by Nanophase Technologies (in 40% dispersion in Finsolv TN, C12-C15 alcohol benzoate);
those marketed under the name "DAITOPERSION ZN-30" and "DAITOPERSION Zn-50" by Daito (dispersions in cyclopolymethylsiloxane/oxyethylenated polydimethylsiloxane, containing 30% or 50% zinc oxides coated with silica and polymethylhydrogen siloxane);
those marketed under the name "NFD Ultrafine ZnO" by Daikin (ZnO coated perfluoroalkyl phosphate and perfluoroalkylethyl-based copolymer in dispersion in cyclopentasiloxane);

those marketed under the name "SPD-Z1" by Shin-Etsu (ZnO coated with silicone-grafted acrylic polymer, dispersed in cyclodimethylsiloxane);

those marketed under the name "Escalol Z100" by ISP (ZnO treated with alumina and dispersed in the ethylhexyl methoxycinnamate/PVP-hexadecene copolymer/methicone mixture);

those marketed under the name "Fuji ZnO-SMS-10" by Fuji Pigment (ZnO coated with silica and polymethylsilsesquioxane);

those marketed under the name "Nanox Gel TN" by Elementis (ZnO in 55% dispersion in C12-C15 alcohol benzoate with hydroxystearic acid polycondensate).

The uncoated cerium oxide pigments are sold for example under the name "COLLOIDAL CERIUM OXIDE" by RHONE POULENC.

The uncoated iron oxide pigments are for example sold by ARNAUD under the names "NANOGARD WCD 2002 (FE 45B)", "NANOGARD IRON FE 45 BL AQ", "NANOGARD FE 45R AQ, "NANOGARD WCD 2006 (FE 45R)", or by MITSUBISHI under the name "TY-220".

The coated iron oxide pigments are for example sold by ARNAUD under the names "NANOGARD WCD 2008 (FE 45B FN)", "NANOGARD WCD 2009 (FE 45B 556)", "NANOGARD FE 45 BL 345", "NANOGARD FE 45 BL", or by BASF under the name "TRANSPARENT IRON OXIDE".

It is also possible to cite metal oxide mixtures, particularly of titanium dioxide and cerium dioxide, including the mixture of equal weights of titanium dioxide and cerium dioxide coated with silica, sold by IKEDA under the name "SUN-VEIL A", and the mixture of titanium dioxide and zinc dioxide coated with alumina, silica and silicone such as the product "M 261" sold by KEMIRA or coated with alumina, silica and glycerin such as the product "M 211" sold by KEMIRA.

The pigments may be introduced into the compositions according to the invention as is or in pigment paste form, i.e. in a mixture with a dispersion agent, as described for example in the document GB-A-2206339.

According to a preferred embodiment, the composition according to the invention comprises a mineral UV filter chosen from the following INCI filter names:

Silica (and) Titanium dioxide,
Titanium dioxide,
Titanium dioxide (and) aluminum hydroxide (and) stearic acid,
Styrene/acrylates copolymer (and) titanium dioxide (and) methyl methacrylate crosspolymer (and) aluminum hydroxide (and) stearic acid, and
any of the mixtures thereof.

According to an embodiment the composition according to the invention comprises titanium oxide as a UV filter.

According to an embodiment, the mineral filter content according to the invention is from 1 to 20%, advantageously from 1 to 15% and preferentially from 1 to 10% by weight based on the total weight of the composition.

According to an embodiment the composition according to the invention comprises a mixture of UV filters of a mineral and organic nature among those mentioned hereinabove.

According to an embodiment the composition comprises as a UV filter at least one UV filter chosen from organic lipophilic UV filters, organic hydrophilic UV filters, organic insoluble organic UV filters, mineral filters or any of the mixtures thereof.

According to an embodiment the composition according to the invention comprises a lipophilic UV filter preferably chosen from drometrizole trisiloxane, diethylamino hydroxybenzoyl hexyl benzoate, ethylhexyltriazone and any one of the mixtures thereof.

Surfactant Having a HLB Greater Than 10

Advantageously, the composition according to the invention comprises at least one surfactant having a HLB greater than 10.

According to an embodiment, the composition according to the invention comprises one or several surfactants having a HLB greater than 10 chosen from non-ionic and anionic surfactants.

In particular the non-ionic surfactants are preferably chosen from:

ethers of glycerol oxyalkylene, in particular oxyethylene and/or oxypropylene, which may contain from 5 to 100 oxyethylene and/or oxypropylene units, preferably 20 to 80 oxyethylene and/or oxypropylene units;

oxyethylene alcohols, in particular oxyethylene and/or oxypropylene, which may contain from 5 to 100 oxyethylene and/or oxypropylene units, preferably from 20 to 100 oxyethylene units, in particular fatty alcohols, in particular in $C_8$-$C_{24}$, and preferably in $C_{12}$-$C_{18}$, ethoxylated such as ethoxylated stearyl alcohol at 20 oxyethylene units (CTFA name "Steareth-20") such as BRIJ 78 sold by UNIQEMA, ethoxylated cetearyl alcohol with 20 oxyethylene groups (CTFA name "Ceteth-20"), ethoxylated stearyl alcohol with 30 oxyethylene units (CTFA name "Ceteareth-30") and the mixture of fatty alcohols in $C_{12}$-$C_{15}$ comprising 7 oxyethylene units (CTFA name "$C_{12-15}$ Pareth-7") such as that marketed under the trade name NEODOL 25-7® by SHELL CHEMICALS;

fatty acid esters, in particular in $C_8$-$C_{24}$, and preferably in $C_{16}$-$C_{22}$, and of polyethylene glycol (or PEG) (which may contain from 5 to 100 oxyethylene units, preferably from 20 to 80 oxyethylene units), such as PEG-50 stearate and PEG-40 monostearate sold under the name MYRJ 52P® by UNIQEMA, or PEG-75 stearate;

fatty acid esters, in particular in $C_8$-$C_{24}$, and preferably in $C_{16}$-$C_{22}$, and ethers of glycerol oxyalkylene, in particular oxyethylene and/or oxypropylene (which may contain from 5 to 100 oxyethylene and/or oxypropylene units), such as monostearate of glyceryle polyoxyethylene with 200 oxyethylene units, sold under the name Simulsol 220 TM® by SEPPIC; stearate of glyceryl polyoxyethylene with 30 motifs oxyethylene units such as the product TAGAT S® sold by GOLDSCHMIDT, oleate of glyceryl polyoxyethylene with 30 oxyethylene units such as the product TAGAT O® sold by GOLDSCHMIDT, cocoate of glyceryl polyoxyethylene with 30 oxyethylene units such as the product VARIONIC LI 13® sold by SHEREX, isostearate of glyceryl polyoxyethylene with 30 oxyethylene units such as the product TAGAT L® sold by GOLDSCHMIDT and laurate of glyceryl polyoxyethylene with 30 oxyethylene units such as the product TAGAT I® by GOLDSCHMIDT;

fatty acid esters, in particular in $C_8$-$C_{24}$, and preferably in $C_{16}$-$C_{22}$, and of sorbitol advantageously oxyalkylene, in particular oxyethylene and/or oxypropylene (which may contain from 5 to 100 oxyethylene and/or oxypropylene units), such as polysorbate 60 in particular sold under the name Tween 60® by UNIQEMA and more particularly mono-laurate of sorbitan oxyethylene with 20 moles of ethylene oxide (INCI name=Polysorbate-20) in particular sold under the name Tween 20® by UNIQEMA;

silicone surfactants, such as for example bis-PEG/PPG-16/16 PEG/PPG-16/16 dimethicone (INCI name), sold for example under the trade name Abil Care 85 by GOLDSCHMIDT, PEG-12 dimethicone (INCI name) sold for example under the trade name Silsoft 880 by Momentive performance materials.

dimethicone copolyol benzoate such as the one sold under the name FINSOLV SLB 101® and 201® by FINTEX;

copolymers of propylene oxide and of ethylene oxide, also called OE/OP polycondensates, and mixtures thereof.

The OE/OP polycondensates are more specifically copolymers consisting of polyethylene glycol and polypropylene glycol blocks, such as, for example polyethylene glycol/polypropylene glycol/polyethylene glycol triblock polycondensates. These triblock polycondensates have, for example, the following chemical structure:

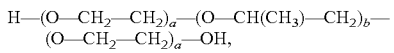

in which formula a ranges from 2 to 120, and b ranges from 1 to 100.

The OE/OP polycondensates preferably have a mean molar mass ranging from 1,000 to 15,000, and better ranging from 2,000 to 13,000. Advantageously, said OE/OP polycondensates have a cloud temperature, with 10 g/l in distilled water, greater than or equal to 20° C., preferably greater than or equal to 60° C. The cloud temperature is measured according to the standard ISO 1065. As OE/OP polycondensate that can be used according to the invention, mention may be made of polyethylene glycol/polypropylene glycol/polyethylene glycol triblock polycondensates sold under the names SYNPERONIC® such as SYNPERONIC PE/L44® and SYNPERONIC PE/F1270 by ICI. In particular the anionic surfactants are preferably chosen from:

gemini surfactants such as for example disodium ethylene dicocamide PEG-15 disulfate (INCI name) sold for example under the trade name CERALUTION H.

salts, in particular alkali metal salts, in particular sodium, ammonium salts, amine salts such as aminoalcohol salts or alkaline earth metal salts such as magnesium, of the following compounds:

alkylsulfates, alkylethersulfates, alkylamidoethersulfates, alkylaryl-polyethersulfates, monoglyceride sulfates;

alkylsulfonates, alkylamidesulfonates, alkylarylsulfonates, α-olefin-sulfonates, paraffin-sulfonates;

alkylphosphates, alkyletherphosphates;

alkylsulfosuccinates, alkylethersulfosuccinates, alkylamide-sulfosuccinates; alkylsulfosuccinamates;

alkylsulfoacetates;

acylsarcosinates; acylisethionates and N-acyltaurates;

fatty acid salts such as oleic, ricinoleic, palmitic, stearic acids, coconut oil or hydrogenated coconut oil acids;

salts of alkyl D galactoside uronic acids;

acyl-lactylates;

salts of alkylether carboxylic polyoxyalkylene acids, of alkylarylether carboxylic polyoxyalkylene acids, of alkylamidoether carboxylic polyoxyalkylene acids, in particular those containing from 2 to 50 ethylene oxide groups;

and mixtures thereof.

Note that the alkyl or acyl radical of these various compounds advantageously comprise from 6 to 24 carbon atoms, and preferably from 8 to 24 carbon atoms, and the aryl radical designating preferably a phenyl or benzyl group.

Use will be made preferably of alkyl(C12-C20) phosphate and in particular a cetylphosphate for example potassium such as that sold for example under the trade name AMPHISOL K.

According to an embodiment, the surfactant having a HLB greater than 10 is a fatty acid salt in C12-C20 such as triethanolamine stearate and any of the mixtures thereof.

According to an embodiment, the surfactant having a HLB greater than 10 is chosen from polysorbate 20, bis-PEG/PPG-16/16 PEG/PPG-16/16 dimethicone, PEG-12 dimethicone, disodium ethylene dicocamide PEG-15 disulfate, potassium cetyl phosphate, TEA stearate, and any of the mixtures thereof.

In one preferred embodiment, the cosmetic composition according to the invention contains polysorbate 20.

According to an embodiment, the content in one or several surfactants having a HLB greater than 10 according to the invention is from 0.1 to 10%, preferably from 0.1 to 5% and advantageously from 0.2 to 3%, preferably from 0.5 to 2% based on the total weight of the composition. In one embodiment, the content of one or more surfactant(s) having a HLB greater than 10 is comprised between 0.2% and 10% by weight, based on the total weight of the composition.

Hydrophilic Gelling Agent

The composition according to the invention comprises at least one hydrophilic gelling agent. Use will be made in particular of aqueous gelling agents and structuring agents conventionally used by those skilled in the art. These gelling agents can be particulate or not, synthetic or of natural origin.

As hydrophilic gelling agents, mention can be made for example of carboxyvinyl polymers such as Carbopols (Carbomers) and Pemulens (acrylate/C10-C30-alkylacrylate copolymer); polyacrylamides such as for example cross-linked copolymers sold under the names Sepigel 305 (C.T.F.A. name: polyacrylamide/C13-14 isoparaffin/Laureth 7) or Simulgel 600 (C.T.F.A. name: acrylamide/sodium acryloyldimethyltaurate copolymer/isohexadecane/polysorbate 80) by Seppic; 2-acrylamido 2-methylpropane sulfonic acid polymers and copolymers, optionally cross-linked and/or neutralized, such as poly(2-acrylamido 2-methylpropane sulfonic acid) marketed by Hoechst under the trade name "Hostacerin AMPS" (CTFA name: ammonium polyacryloyldimethyl taurate or SIMULGEL 800 marketed by SEPPIC (CTFA name: sodium polyacryolyldimethyl taurate/polysorbate 80/sorbitan oleate); 2-acrylamido 2-methylpropane sulfonic acid and hydroxyethyl acrylate copolymers such as SIMULGEL NS and SEPINOV EMT 10 marketed by SEPPIC; cellulose derivatives such as hydroxyethylcellulose; polysaccharides and particularly gums such as Xanthan gum; and mixtures thereof.

According to an embodiment, the hydrophilic gelling agent comprises at least one xanthan gum.

According to a preferred embodiment, the hydrophilic gelling agent comprises at least acrylamide/sodium acryloyldimethyltaurate copolymer, possibly as an inverse emulsion. An inverse emulsion can be used such as Simulgel 600 (INCI name.: acrylamide/sodium acryloyldimethyltaurate copolymer/isohexadecane/polysorbate 80) by Seppic.

According to an embodiment, the hydrophilic gelling agent is a mixture of one or several of the compounds listed hereinabove.

According to an embodiment, the hydrophilic gelling agent is chosen from xanthan gum, copolymers of acrylamide and acryloyldimethyltaurate of sodium and mixtures thereof.

According to an embodiment, the active material content of the hydrophilic gelling agent is from 0.1 to 5%, advantageously from 0.2 to 2% and possibly from 0.5 to 1.5% based on the total weight of the composition.

The compositions in accordance with this invention can further comprise conventional cosmetic adjuvants particularly selected from routine cosmetic additives: pigments, mineral fillers, dyes, active constituents, etc.

The compositions in accordance with this invention can further comprise biological constituents (anti-aging, oily skin, whitening, anti-stain, antiperspirants, anti-oxidants in particular), infra-red filters, film-forming polymers, scattering fillers, oils, fats such as for example fatty alcohols, moisturizers, emollients, etc.

According to another aspect, the invention relates to a method for preparing the composition according to the invention.

According to an embodiment, the method for preparing a composition according to the invention comprises the following steps (a), (b) and (c):

Step (a), Comprising the Sub-Steps:
(i) of mixing M1 of at least one monoglyceride, at least one tartaric ester of monoglyceride of fatty acids and at least water,
(ii) possibly of increasing the temperature of said mixture,
(iii) of maintaining the temperature of said mixture over time at a temperature higher than the ambient temperature,
(iv) decreasing the temperature of said mixture, possibly by adding a liquid at an ambient temperature, and
(v) the possible adding of at least one hydrophilic gelling agent.

Step (b), Comprising the Sub-Steps:
(i) of mixing M2 of at least one UV filter and a solvent,
(ii) possibly of increasing the temperature of said mixture,
(iii) of maintaining the temperature of said mixture over time at a temperature higher than the ambient temperature,
(iv)—adding of at least one surfactant having a HLB greater than 10, possibly heated beforehand,
(v) the possible adding of a hydrophilic gelling agent, and
(vi) decreasing the temperaure of said mixture,
with at least one of the steps (a)(v) and (b)(v) comprising the adding of a hydrophilic gelling agent.

Step (c) Comprising the Sub-Step of Mixing the Mixtures M1 and M2 Obtained from the Step (a) and from the Step (b).

According to an embodiment of the method according to the invention, the temperature of the mixture during the sub-step (iii) of the step (a) is between 50 and 80° C., advantageously 55 and 65° C.

According to an embodiment of the method according to the invention, the duration of maintaining the temperature during the sub-step (iii) of the step (a) is between 10 min and 2 hours, advantageously between 30 min and one hour.

According to an embodiment of the method according to the invention, the stirring speed during the sub-step (iii) of the step (a) is between 100 and 1000 rpm (rotation per minute), advantageously between 400 and 800 rpm.

According to an embodiment of the method according to the invention, the stirring speed and the temperature during the sub-step (iii) of the step (a) are adjusted in such a way as to obtain a homogeneous and opalescent phase.

According to an embodiment, the liquid added during the sub-step (iv) of the step (a) is or comprises water.

According to an embodiment, the liquid added during the sub-step (iv) of the step (a) is at ambient temperature.

According to an embodiment of the method according to the invention, the stirring speed during the sub-step (iv) of the step (a) is between 1000 and 5000 rpm, advantageously between 2000 and 4000 rpm.

According to an embodiment of the method according to the invention, the cooling to ambient temperature during the sub-step (iv) of the step (a) takes a period of time between 1 and 15 min.

According to an embodiment of the method according to the invention, the hydrophilic gelling agent added during the sub-step (v) of the step (a) is chosen from those mentioned in this invention.

According to an embodiment of the method according to the invention, the temperature of the mixture during the sub-step (iii) of the step (b) is between 60 and 95° C., advantageously 70 and 90° C.

According to an embodiment of the method according to the invention, the duration of maintaining the temperature during the sub-step (iii) of the step (b) is between 10 min and 2 hours, advantageously between 10 min and one hour.

According to an embodiment of the method according to the invention, the stirring speed during the sub-step (iii) of the step (b) is between 100 and 1000 rpm, advantageously between 400 and 800 rpm.

According to an embodiment of the method according to the invention, the HLB surfactant greater than 10 added during the sub-step (iv) of the step (b) is chosen from those mentioned in this invention. This surfactant can be heated beforehand.

According to an embodiment of the method according to the invention, the stirring speed during the sub-step (iv) of the step (b) is between 2000 and 4000 rpm.

According to an embodiment, the hydrophilic gelling agent added during the sub-step (v) of the step (b) is chosen from those mentioned in this invention.

According to an embodiment, during the sub-step (vi) of the step (b), the cooling takes place at slow stirring, with the stirring speed being between 20 and 100 rpm.

According to an embodiment, during the step (c), the mixture is stirred until a homogeneous smooth and/or glossy phase is obtained.

According to an embodiment, the step (b) consists in the emulsification of the filters.

Advantageously, the step (a) consists in the formation of a coagel.

The method according to the invention can further comprise one sub-step or sub-steps or steps inserted into the method at any location. The step (a) can be carried out before the step (b).

According to an embodiment of the method according to the invention, the temperature of the mixture during the sub-step (iii) of the step (a) and/or (b) is between 55 and 65° C.

According to a third aspect, the invention relates to the use of a composition according to the invention to protect from the rays of the sun a body area, in particular a skin area, of a human being.

According to a fourth aspect, the invention relates to a method of protecting from the rays of the sun, with said method comprising the application of a composition according to the invention on a body area, in particular a skin area, of a human being. This invention will now be described more specifically through examples that are in no way limiting of the scope of the invention. However, the examples provide information about specific characteristics, variants and embodiments of the invention.

The expression "between . . . and . . . " includes the limits mentioned. According to an alternative, this expression excludes the limits mentioned.

The expression "according to the invention" designates this description including all of the specific characteristics, alternatives and embodiments, taken independently or in any combination thereof.

The expression "and in any of their mixtures thereof" covers any mixture of two, several or of all of the species described.

In the examples, the temperature is given in degrees Celsius and is the ambient temperature (23° C.), unless mentioned otherwise, and the pressure is the atmospheric pressure at sea level unless mentioned otherwise. Furthermore, percentages are given in mass relative to the total mass, unless mentioned otherwise.

EXAMPLES

Example 1

Cosmetic Composition and the Method for Preparing it According to the Invention

Cosmetic Composition

| Phase | INCI name (possible comment) | Trade name | mass % |
|---|---|---|---|
| A | GLYCERYL STEARATE (Monoglyceride) | TEGIN 90 PELLETS | 6 |
|   | DIACETYL TARTARIC ACID ESTERS OF MONO AND DIGLYCERIDES OF FATTY ACIDS | PANODAN A2020 MB | 0.2 |
|   | WATER |   | 24.98 |
|   | PHENOXYETHANOL |   | 0.5 |
|   | DISODIUM EDTA |   | 0.1 |
| B | CITRIC ACID |   | 0.05 |
|   | PROPYLENE GLYCOL |   | 2 |
|   | GLYCERIN |   | 5 |
| C | TITANIUM DIOXIDE (UV filter) | MICRO TITANIUM DIOXIDE MT-900Z | 3 |
| D | WATER |   | 19.92 |
| E | XANTHAN GUM | KELTROL CG-T | 0.2 |
|   | ACRYLAMIDE/SODIUM ACRYLOYLDIMETHYLTAURATE COPOLYMER | SIMULGEL 600 | 1 |
| F | C12-15 ALKYL BENZOATE | FINSOLV TN | 10 |
|   | DROMETRIZOLE TRISILOXANE (UV filter) | SILATRIZOLE | 2 |
|   | DIETHYLAMINO HYDROXYBENZOYL HEXYL BENZOATE (UV filter) | UVINUL A PLUS GRANULAR | 3 |
|   | ETHYLHEXYL TRIAZONE (UV filter) | UVINUL T 150 | 2.5 |
|   | WATER |   | 17.55 |
|   | POLYSORBATE 20 (HLB surfactant greater than 10) | TWEEN 20 | 1 |
|   | ACRYLAMIDE/SODIUM ACRYLOYLDIMETHYLTAURATE COPOLYMER (Hydrophilic gelling agent) | SIMULGEL 600 | 1 |
|   | total |   | 100 |

Methods for Preparing:

Step (a), Starting from Phases A, B, C, D and E
1. Fill the mixture of phases A+B+C in a melter, keep the temperature at 65° C. for 45 minutes with stirring at 600 rpm until a homogeneous and opalescent phase.
2. Stop the flow of heat and add D at ambient temperature in order to quickly cool with vigorous stirring between 2000 and 4000 rpm.
3. Add E with stirring at ambient temperature.

Step (b), (Phase F)
1. Introduce the UV filters and the solvent in a melter, maintain the temperature at 80° C. for 15 mins with stirring 600 rpm.
2. Add in 1. the water and the surfactant heated beforehand to 70° C. under vigorous stirring between 2000 and 4000 rpm for 15 mins.
3. Add the hydrophilic gelling agent with vigorous stirring between 2000 and 4000 rpm for 2 mins.
4. Cool with slow stirring with coaxial blades 90 rpm and scraping 30 rpm.

Step (c)
Place the two phases obtained in the step (a) and the step (b) in the tank and mix with slow stirring with coaxial blades 90 rpm and scraping 30 rpm for 15 mins until a homogeneous, smooth and glossy phase is obtained.

Example 2 and Comparative Example A

Cosmetic Compositions and Associated Performance in Photoprotection

Cosmetic Composition:

| Phase | INCI name (possible comment) | Ex. 2 | Ex. A |
|---|---|---|---|
| A | GLYCERYL STEARATE (Monoglyceride) | 6 |   |
|   | DIACETYL TARTARIC ACID ESTERS OF MONO AND DIGLYCERIDES OF FATTY ACIDS | 0.2 | 0.2 |
|   | WATER | 63.50 | 60.50 |
|   | PHENOXYETHANOL | 0.5 | 0.5 |
|   | DISODIUM EDTA | 0.1 | 0.1 |
| B | PROPYLENE GLYCOL | 2 | 2 |
|   | GLYCERIN | 5 | 5 |
| C | GLYCERYL STEARATE (Monoglyceride) |   | 6 |
|   | PEG-30 DIPOLYHYDROXYSTEARATE CITHROL DPHS-SO-(MV) CRODA |   | 3 |
|   | TITANIUM DIOXIDE MT-100 T V from TAYCA | 3 | 3 |
|   | C12-15 ALKYL BENZOATE (solvent) | 10 | 10 |
|   | DROMETRIZOLE TRISILOXANE (UV filter) | 2 | 2 |
|   | DIETHYLAMINO HYDROXYBENZOYL HEXYL BENZOATE (UV filter) | 3.0 | 3.0 |
|   | ETHYLHEXYL TRIAZONE (UV filter) | 2.5 | 2.5 |
| D | XANTHAN GUM | 0.2 | 0.2 |
| E | ACRYLAMIDE/SODIUM ACRYLOYLDIMETHYLTAURATE COPOLYMER (SIMULGEL 600 | 2 | 2 |
|   | Total | 100 | 100 |

Properties of the Formulas After 24 h:

|  | Example 2 | Example A |
|---|---|---|
| Aspect | Fluid cream | Thick and non-glossy cream |
| Microscopy | Crystal dispersion | Emulsion |
| SPF measured in Vitro | 95.63 | 42.85 |

Methods for Preparing:

The method of the formula of example 2 is similar to that of example 1.

It consists in forming a hot fatty lamellar phase then in incorporating therein the UV filters just before the drop in temperature (65°).

In comparison, if the UV filters and the glyceryl stearate are emulsioned as a wax thanks to the adding of a surfactant such as CITHROL DPHS-SO-(MV) CRODA of HLB such that 5<HLB<6 (Example A), an different organization of the fatty phase of coagel is obtained, which does not make it possible to obtain as good photoprotection as in example 2 (shown by the value of SPF).

Example 3

Improvement in the Stability of the Composition by Adding a Surfactant Having a HLB Greater Than 10. (Comparative Composition (ex.3) Compared to Example 1)

| Phase | INCI name (possible comment) | Ex. 3 (comparison) | Ex. 1 |
|---|---|---|---|
| A | GLYCERYL STEARATE (Monoglyceride) | 6 | 6 |
|  | DIACETYL TARTARIC ACID ESTERS OF MONO AND DIGLYCERIDES OF FATTY ACIDS | 0.2 | 0.2 |
|  | WATER | 24.98 | 24.98 |
|  | PHENOXYETHANOL | 0.5 | 0.5 |
|  | DISODIUM EDTA | 0.1 | 0.1 |
| B | CITRIC ACID (for adjusting the pH) | 0.00 | 0.05 |
|  | PROPYLENE GLYCOL | 2 | 2 |
|  | GLYCERIN | 5 | 5 |
| C | TITANIUM DIOXIDE (UV filter) | 3 | 3 |
| D | WATER | 20.97 | 19.92 |
| E | XANTHAN GUM | 0.2 | 0.2 |
|  | ACRYLAMIDE/SODIUM ACRYLOYLDIMETHYLTAURATE COPOLYMER (SIMULGEL 600) | 1 | 1 |
| F | C12-15 ALKYL BENZOATE (solvent) | 10 | 10 |
|  | DROMETRIZOLE TRISILOXANE (UV filter) | 2 | 2 |
|  | DIETHYLAMINO HYDROXYBENZOYL HEXYL BENZOATE (UV filter) | 3 | 3 |
|  | ETHYLHEXYL TRIAZONE (UV filter) | 2.5 | 2.5 |
|  | WATER | 17.55 | 17.55 |
|  | POLYSORBATE 20 (HLB surfactant greater than 10) |  | 1 |
|  | ACRYLAMIDE/SODIUM ACRYLOYLDIMETHYLTAURATE COPOLYMER (and) ISOHEXADECANE (and) POLYSORBATE 80 (Hydrophilic gelling agent) | 1 | 1 |
|  | total | 100 | 100 |
|  | Comments | Unstable dispersion and non-homogeneous application | Stable dispersion and homogeneous application |

Methods for Preparing:

The method of the formula of example 1 is described precisely in example 1 hereinabove. It consists in first forming during the step called (a) that fatty phase of coagel. During the step called (b), an emulsion of the UV filters is carried out, thanks to the adding of a surfactant having a HLB greater than 10. During the step (c), the emulsion obtained during the step (b) can then be introduced extemporaneously, at ambient temperature, in the fatty phase of coagel obtained during the step (a).

The formula of example 1 is stable over time, i.e. it remains homogeneous over time and its performance, in particular with regards to photoprotection, does not change over time.

Contrary to example 1, in example 3, the UV filters of the phase F were introduced in step (a) of the formation of the fatty phase of coagel. There is therefore no separate step (a), (b) and (c). In addition, the composition according to example 3 does not contain any surfactant having a HLB greater than 10, such as for example polysorbate 20.

The formula of example 3 is not homogeneous to the application (impurity), or over time. It is unstable over time contrary to the formula of example 1.

This example shows the importance of the surfactant having a surfactant greater than 10 and of the associated method of manufacture, which makes it possible to obtain a stable dispersion and a homogeneous application.

Example 4

Improvement in the Performance in Terms of Photoprotection of the Composition Thanks to the Tartaric Ester of Monoglyceride of Fatty Acids. (Comparative Composition (ex.4) Compared to the Example 1)

| Phase | INCI name (possible comment) | Ex. 4 | Ex. 1 |
|---|---|---|---|
| A | GLYCERYL STEARATE (Monoglyceride) | 6 | 6 |
|  | DIACETYL TARTARIC ACID ESTERS OF MONO AND DIGLYCERIDES OF FATTY ACIDS |  | 0.2 |

-continued

| Phase | INCI name (possible comment) | Ex. 4 | Ex. 1 |
|---|---|---|---|
| | STEARIC/ ACID | 0.1 | |
| | TRIETHANOLAMINE | 0.05 | |
| | WATER | 24.91 | 24.98 |
| | PHENOXYETHANOL | 0.5 | 0.5 |
| | DISODIUM EDTA | 0.1 | 0.1 |
| B | CITRIC ACID (for adjusting the pH) | 0.03 | 0.05 |
| | PROPYLENE GLYCOL | 2 | 2 |
| | GLYCERIN | 5 | 5 |
| C | TITANIUM DIOXIDE (UV filter) | 3 | 3 |
| D | WATER | 19.92 | 19.92 |
| E | XANTHAN GUM | 0.2 | 0.2 |
| | ACRYLAMIDE/SODIUM ACRYLOYLDI-METHYLTAURATE COPOLYMER (and) ISOHEXADECANE (and) POLYSORBATE 80 | 1 | 1 |
| F | C12-15 ALKYL BENZOATE (solvent) | 10 | 10 |
| | DROMETRIZOLE TRISILOXANE (UV filter) | 2 | 2 |
| | DIETHYLAMINO HYDROXYBENZOYL HEXYL BENZOATE (UV filter) | 3 | 3 |
| | ETHYLHEXYL TRIAZONE (UV filter) | 2.5 | 2.5 |
| | WATER | 17.55 | 17.55 |
| | POLYSORBATE 20 (HLB surfactant greater than 10) | 1 | 1 |
| | ACRYLAMIDE/SODIUM ACRYLOYLDIMETHYLTAURATE COPOLYMER (and) ISOHEXADECANE (and) POLYSORBATE 80 (Hydrophilic gelling agent) | 1 | 1 |
| | total | 100 | 100 |

Methods for preparing: the methods for preparing of the example 1 and 4 are identical between them and identical to the method described in example 1. The formulas of examples 1 and 4 are stable over time.

However, the performance in terms of photoprotection of the formula of example 1 is much higher than that of example 4. Indeed, the SPF measured (in vivo) is 46.7 for example 1 compared to 28.1 for example 2.

This example shows the importance of the Tartaric ester of monoglyceride of fatty acids in the composition according to the invention. It makes it possible to obtain an improvement in the photoprotection.

The invention claimed is:

1. A composition that comprises
A) a coagel phase that comprises
   I) at least one monoglyceride,
   II) at least one tartaric ester of monoglycerides based on C12-C22 fatty acids
   III) water,
B) at least one UV filter,
C) at least one surfactant having a HLB greater than 10, and
D) at least one hydrophilic gelling agent;
wherein the content of said at least one surfactant having a HLB greater than 10 is between 0.2% and 10% by weight, based on the total weight of the composition, wherein the composition comprises a monoglyceride content from 1% to 20% by weight based on the total weight of said composition, and wherein the tartaric ester of monoglyceride content ranges from 0.05% to 2% by weight based on the total weight of said composition.

2. The composition, according to claim 1, which comprises an aqueous phase.

3. The composition, according to claim 1, which comprises as a monoglyceride one or more monoglycerides comprising an alkyl chain, saturated or unsaturated, comprising from 12 to 22 carbon atoms.

4. The composition, according to claim 1, wherein the monoglyceride comprises an alkyl chain, saturated or unsaturated, comprising from 16 to 18 carbon atoms.

5. The composition, according to claim 1, wherein the composition comprises monoglyceride content from 2% to 10 by weight based on the total weight of said composition.

6. The composition, according to claim 1, wherein the tartaric ester of monoglycerides of fatty acids is a diacetyl tartaric ester of monoglyceride comprising an alkyl chain, saturated or unsaturated, comprising from 12 to 22 carbon atoms.

7. The composition, according to claim 1, wherein the tartaric ester of monoglyceride content ranges from 0.1% to 1% by weight based on the total weight of said composition.

8. The composition, according to claim 1, wherein the composition comprises as a UV filter at least one UV filter chosen from organic lipophilic UV filters, organic hydrophilic UV filters, insoluble organic UV filters, mineral filters or any of the mixtures thereof.

9. The composition, according to claim 1, wherein the UV filter comprises a lipophilic UV filter.

10. The composition, according to claim 1, wherein the surfactant having a HLB greater than 10 is chosen from polysorbate 20, bis-PEG/PPG-16/16 PEG/PPG-16/16 dimethicone, PEG-12 dimethicone, disodium ethylene dicocamide PEG-15 disulfate, potassium cetyl phosphate, TEA stearate, and any of the mixtures thereof.

11. The composition, according to claim 1, wherein the hydrophilic gelling agent is chosen from xanthan gum, copolymers of acrylamide and acryloyldimethyltaurate of sodium and mixtures thereof.

12. A method for preparing a composition according to claim 1, which comprises the following steps (a), (b) and (c):
Step (a), comprising the sub-steps:
   (i) of mixing M1 of at least one monoglyceride, at least one tartaric ester of monoglyceride of fatty acids and at least water,
   (ii) possibly of increasing the temperature of said mixture,
   (iii) of maintaining the temperature of said mixture over time at a temperature higher than the ambient temperature,
   (iv) decreasing the temperature of said mixture, optionally by adding a liquid at an ambient temperature, and
   (v) the possible adding of at least one hydrophilic gelling agent;
Step (b), comprising the sub-steps:
   (i) of mixing M2 of at least one UV filter and a solvent,
   (ii) optionally of increasing the temperature of said mixture,
   (iii) of maintaining the temperature of said mixture over time at a temperature higher than the ambient temperature,
   (iv) adding of at least one surfactant having a HLB greater than 10, optionally heated beforehand,
   (v) optionally adding a hydrophilic gelling agent, and
   (vi) decreasing the temperature of said mixture,
   with at least one of the steps (a)(v) and (b)(v) comprising the adding of a hydrophilic gelling agent;
Step (c) comprising the sub-step of mixing the mixtures M1 and M2 coming from the step (a) and from the step (b).

13. The method according to claim 12, wherein-the temperature of the mixture during the sub-step (iii) of the step (a) and/or (b) is between 55 and 65° C.

14. A method for protecting from the rays of the sun, which comprises applying a composition according to claim 1 on a body area of a human being.

15. A method for protecting from the rays of the sun, which comprises applying a composition according to claim 1 a skin area, of a human being.

16. The composition, according to claim 2, which comprises as a monoglyceride one or more monoglycerides comprising an alkyl chain, saturated or unsaturated, comprising from 12 to 22 carbon atoms.

17. The composition, according to claim 2, wherein the monoglyceride comprises an alkyl chain, saturated or unsaturated, comprising from 16 to 18 carbon atoms.

18. The composition, according to claim 3, wherein the monoglyceride comprises an alkyl chain, saturated or unsaturated, comprising from 16 to 18 carbon atoms.

19. The composition, according to claim 2, wherein the composition comprises monoglyceride content from 2% to 10% by weight based on the total weight of said composition.

20. The composition, according to claim 1, wherein the UV filter is chosen from drometrizole trisiloxane, diethylamino hydroxybenzoyl hexyl benzoate, ethylhexyltriazone and any of the mixtures thereof.

\* \* \* \* \*